(12) United States Patent
Grande

(10) Patent No.: US 10,390,699 B2
(45) Date of Patent: Aug. 27, 2019

(54) DETECTION AND RESPONSE SYSTEM FOR OPIOID OVERDOSES

(71) Applicant: Vincenzo Grande, Bridgewater, NJ (US)

(72) Inventor: Vincenzo Grande, Bridgewater, NJ (US)

(*) Notice: Subject to any disclaimer, the term of this patent is extended or adjusted under 35 U.S.C. 154(b) by 0 days.

(21) Appl. No.: 16/161,801

(22) Filed: Oct. 16, 2018

(65) Prior Publication Data

US 2019/0216317 A1 Jul. 18, 2019

Related U.S. Application Data

(63) Continuation-in-part of application No. 15/873,445, filed on Jan. 17, 2018.

(51) Int. Cl.
```
A61B 5/00      (2006.01)
A61B 5/0205    (2006.01)
A61B 5/08      (2006.01)
G16H 20/17     (2018.01)
G08B 25/01     (2006.01)
A61M 5/20      (2006.01)
```

(52) U.S. Cl.
CPC .......... *A61B 5/0002* (2013.01); *A61B 5/0205* (2013.01); *A61B 5/0816* (2013.01); *A61B 5/4836* (2013.01); *A61B 5/6802* (2013.01); *A61B 5/746* (2013.01); *G08B 25/016* (2013.01); *G16H 20/17* (2018.01); *A61M 5/20* (2013.01)

(58) Field of Classification Search
CPC ............ A61M 5/14244; A61B 5/6823; A61B 5/6824; A61B 5/6813; A61B 5/6814; A61B 5/6815; A61B 5/6816; A61B 5/6817; A61B 5/6819; A61B 5/682; A61B 5/6821; A61B 5/6822; A61B 5/6825
See application file for complete search history.

(56) References Cited

U.S. PATENT DOCUMENTS

| | | | |
|---|---|---|---|
| 3,720,211 A | 3/1973 | Kyrius | |
| 3,791,767 A * | 2/1974 | Shill | A61M 1/106 128/DIG. 3 |
| 6,762,684 B1 | 7/2004 | Camhi | |
| 6,858,020 B2 | 2/2005 | Rosnak | |
| 8,276,877 B2 | 10/2012 | Cha et al. | |
| 8,695,591 B2 | 4/2014 | Olson et al. | |
| 2013/0172759 A1* | 7/2013 | Melker | A61M 5/1723 600/476 |
| 2017/0172522 A1* | 6/2017 | Insler | A61B 5/746 |
| 2018/0200433 A1* | 7/2018 | Cirit | A61M 5/1723 |
| 2018/0333532 A1* | 11/2018 | Wei | A61M 5/14248 |

* cited by examiner

*Primary Examiner* — Phillip A Gray
(74) *Attorney, Agent, or Firm* — Thomas J. Germinario

(57) ABSTRACT

A wearable system detects an opioid overdose and transmits a distress message with the wearer's GPS coordinates to one or more emergency response contacts. Concurrently, the system signals a switch which energizes a solenoid injector, causing a prescribed dosage of an opioid antidote to be injected by a syringe into the wearer's body. Detection of an opioid overdose is based on one or more symptomatic biometrics, which are measured by a wearable monitor. The monitor unit and the injector units can be separate, or they can be combined in a single unit.

7 Claims, 4 Drawing Sheets

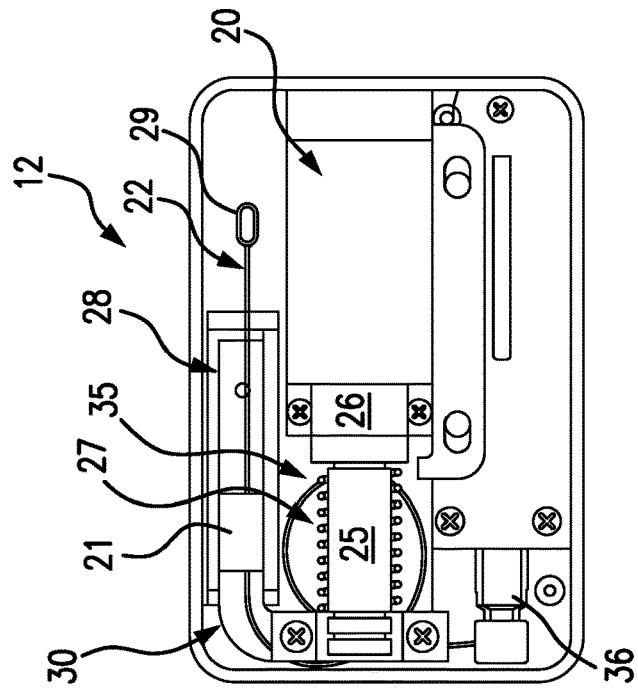
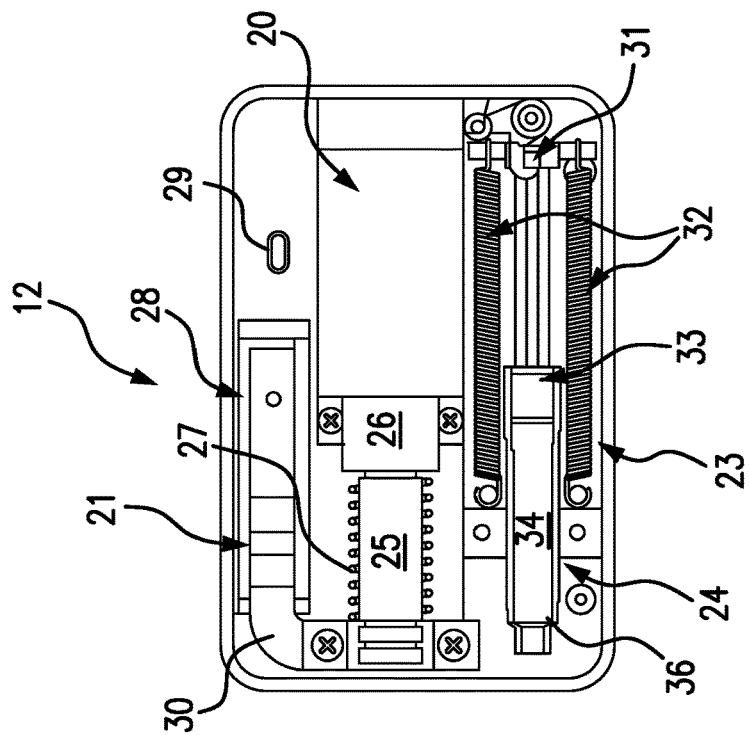
FIG. 3B
FIG. 3A

DETECTION AND RESPONSE SYSTEM FOR OPIOID OVERDOSES

REFERENCE TO RELATED APPLICATION

This application is a continuation-in-part of U.S. Non-Provisional Utility patent application Ser. No. 15/873,445, filed Jul. 19, 2018, which is incorporated herein by reference.

FIELD OF INVENTION

The present invention relates to the fields of systems for remotely monitoring the vital signs of a subject and for initiating emergency response measures when monitored vital signs indicate a life-threatening situation.

BACKGROUND OF THE INVENTION

In recent years, deaths from overdoses of opioid drugs have reached epidemic proportions, claiming tens of thousands of lives each year. Wearable GPS devices are available to track the whereabouts of drug abusers and to monitor vital signs, such as depressed respiratory and heart rates, which are indicative of an opioid overdose. Once an overdose situation is detected, however, the time for emergency responders to reach the subject and administer an opioid antidote is often too long to save his/her life. Therefore, there is a need for a system which combines remote detection of an opioid overdose with remote activation of a wearable antidote injection system upon detection of an overdose situation.

SUMMARY OF THE INVENTION

The present invention is a wearable system for detecting an opioid overdose and, upon such detection, transmitting a distress message with the wearer's GPS coordinates to one or more emergency responders. Concurrently with transmitting the message to emergency responders, the system energizes a solenoid.

Upon activation, the armature of the solenoid retracts into the solenoid coil, biasing a return spring and pulling a needle carriage along a track so as to thrust a hypodermic needle through an aperture, inserting it into the body of the wearer. Upon full retraction of the solenoid armature, it opens a latch to release a spring-loaded plunger within a syringe assembly containing a syringe loaded with a prescribed dosage of an opioid antidote. The plunger springs contract, depressing the syringe plunger so as to force the antidote in the syringe out through flexible connection tubing into the inserted needle, which injects the antidote into the wearer's body. Upon the plunger reaching the end of the syringe, it triggers a microswitch or sensor, which causes deactivation of the solenoid, causing the return spring to extract the armature from the solenoid coil. The extracted armature pulls the needle carriage back, so as to withdraw the needle from the wearer's body.

The detection of an opioid overdose in the wearer is based upon measurements of one or more vital signs, which are symptomatic of opioid use including depressed heart rate, depressed respiration rate and elevated blood $CO_2$. Preferably, the system comprises a monitor unit, which is attached to the wearer's body by a band, strap or adhesive strips, and an injector unit, which can be attached to one of the wearer's arms or legs, also by a band, strap or adhesive strips. Optionally, the monitor unit and the injector unit can be combined in a single unit.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

BRIEF DESCRIPTION OF THE DRAWINGS

FIG. 3A is a bottom plan view of a de-energized solenoid injector, according to one embodiment of the present invention;

FIG. 3B is a top plan view of a de-energized solenoid injector, according to one embodiment of the present invention.

DETAILED DESCRIPTION OF THE PREFERRED EMBODIMENT

Figure 1:
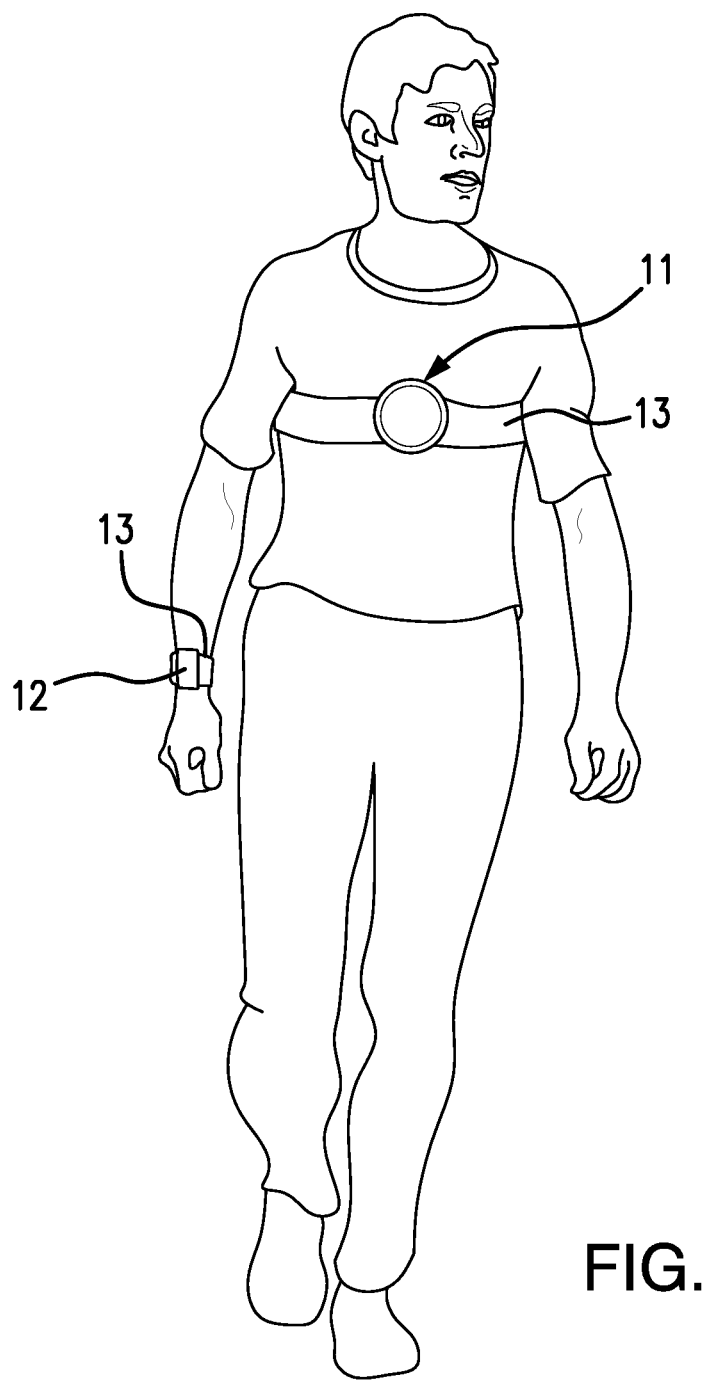
FIG. 1 is a perspective view of one embodiment of the present invention attached to the body of a wearer.
Figure 2:
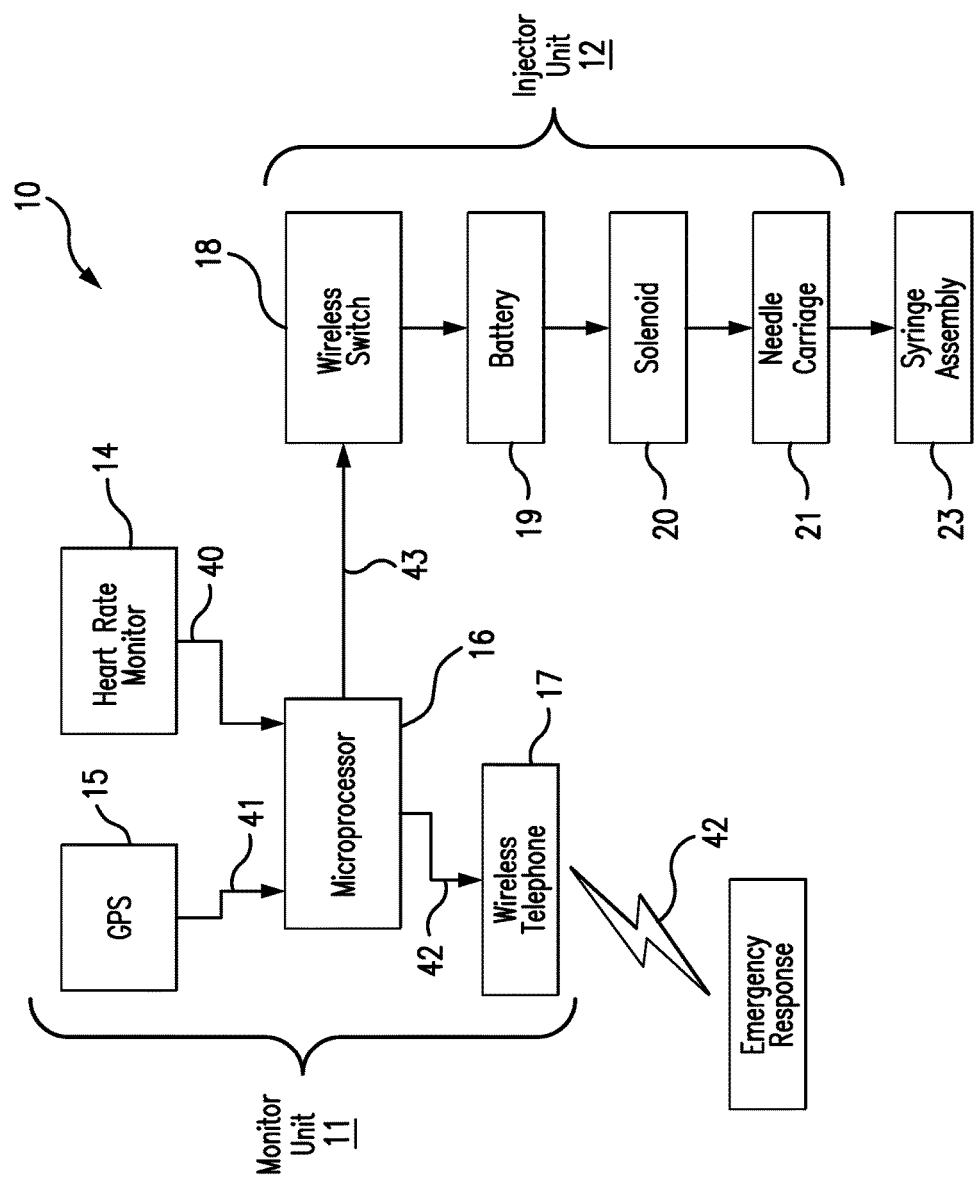
FIG. 2 is a schematic diagram of the components of one embodiment of the present invention and their interaction.

Referring to FIGS. 1 and 2, the preferred embodiment of the present invention 10 consists of a wearable monitor unit 11 and a wearable injector unit 12. The monitor and injector units 11 12 can be separate units removably attached to different parts of the wearer's body, as depicted in FIG. 1, or they can be combined in one unit. The monitoring unit 11 can be worn across the chest, as shown in FIG. 1, supported by a strap, band 13 or adhesive strips, while the injector unit 12 can be worn around one of the wearer's wrists, as depicted in FIG. 1, also supported by a strap, band 13 or adhesive strips.

The monitor unit 11 comprises a heart rate monitor 14, a Global Positioning System (GPS) receiver 15, a monitor microprocessor 16, and a wireless telephone transmitter 17. The components of the monitor unit 11 can be electrically connected to a central battery (not shown) or each component 14-17 can have its own battery. Where the monitor unit 11 and the injector unit 12 are combined in one unit, they can have a shared battery 19. For exemplary purposes, the preferred embodiment 10 uses a heart rate monitor 14, but it should be understood that other biometrics can also be monitored, including respiratory rate and blood $CO_2$.

The injector unit 12 comprises a wireless solenoid switch 18, a battery 19, a solenoid 20, a needle carriage 21 containing a hypodermic needle 22, and a syringe assembly 23 containing a syringe 24 with a prescribed dosage of an opioid antidote 34, such as naloxone hydrochloride. The solenoid switch 18 can be an electro-mechanical switch, an electronic switch or a transistor switch, all of which are well known in the art. While the solenoid switch 18 is wireless in the preferred embodiment 10, if the monitor unit 11 and the injector unit 11 are combined, the solenoid switch 18 need not be wireless.

It should be understood that, while a battery 19 is used as the power source for the injector unit 12 in this exemplary embodiment of the present invention 10, another local electrical power source, such as a charging capacitor, can be substituted for or used with the battery 19.

As best seen in FIGS. 3A and 3B, the solenoid 20 has an armature 25 which retracts into the solenoid core 26 when the solenoid 20 is energized, thereby biasing a return spring 27 and pulling the needle carriage 21 forward along a carriage track 28, so that the hypodermic needle 22 protrudes through a needle aperture 29 and becomes inserted into the wearer's body. The needle carriage 21 is attached to the distal end of the armature 25 by a carriage bracket 30. While the return spring 27 is compressively biased by the retracting armature 25 in the preferred embodiment 10, it should be understood that an alternate configuration of the solenoid 20 would cause the return spring 27 to be extensionally biased by the retracting armature 25. In the latter configuration, the return spring 27 would contract when the solenoid 20 is deactivated, and would pull the armature 25 out of the solenoid core 26.

When the armature 25 of the activated solenoid 20 retracts, it opens a latch 31 which releases a syringe plunger 33 attached to a pair of plunger springs 32 within the syringe assembly 23. The released plunger springs 32 contract, depressing the syringe plunger 33 so as to force the antidote 34 out through the connection tubing 35 and then through the hypodermic needle 22 into the wearer's body. Upon the syringe plunger 33 reaching the distal end of the syringe 24, it triggers a micro-switch or sensor 36, which causes deactivation of the solenoid 20. The return spring 27 then expands, so as to extract the armature 25 from the solenoid core 26. The extracted armature 25 pulls the needle carriage 21 back away from the needle aperture 29, thereby withdrawing the hypodermic needle 22 from the wearer's body.

Where a sensor 36 is used in deactivating the solenoid 20, the injector unit 12 can further comprise an injector microprocessor (not shown) which communicates with the sensor 36 and controls the solenoid switch 18, and which is programmed to open the solenoid switch 18 and de-energize the solenoid 20 upon receiving a signal from the sensor 36 when the syringe plunger 33 is fully depressed. Alternately, the injector microprocessor can be programmed to open the solenoid switch 18 and de-energize the solenoid switch 20 after a pre-set time interval following the insertion of the hypodermic needle 22 into the wearer's body.

The heart rate monitor 14 continuously monitors the wearer's heart rate and continuously transmits 40 the wearer's heart rate, preferably in a digital format, to the monitor microprocessor 16. The monitor microprocessor 16 is programmed to continuously compare the wearer heart rate with a pre-set threshold heart rate indicative of an opioid overdose. Upon determining that the wearer's heart rate is below the threshold heart rate, the monitor microprocessor 16 is programmed to obtain the wearer's current location coordinates 41 from the GPS receiver 15, and to send one or more emergency distress messages 42 to one or more emergency contacts, using the wireless telephone transmitter 17. The emergency messages 42 can be voice, text or a combination of both.

Upon determining that the wearer's heart rate is below the threshold heart rate, the monitor microprocessor 16 is also programmed to wirelessly transmit an activation signal 43 to the wireless solenoid switch 18 of the injector unit 12. Upon receiving the activation signal 43, the solenoid switch 18 is configured to complete an energizing circuit by which the battery 19 energizes the solenoid 20.

Figure 4:
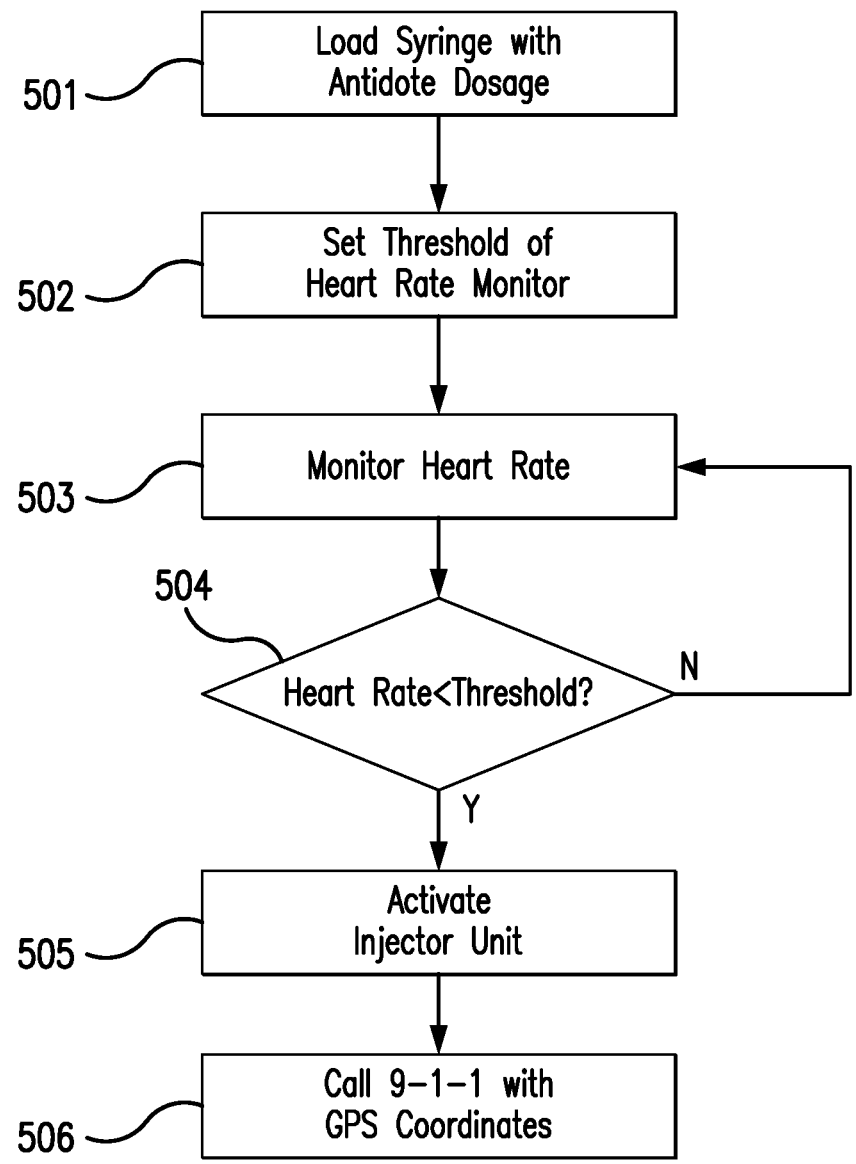
FIG. 4 is a flow chart depicting the operation of one embodiment of the present invention.

FIG. 4 depicts the process by which the system 10 is employed. The syringe is filled with the antidote dosage 501. The threshold heart rate is set in the heart rate monitor 502. The heart rate is then monitored 503, and when determined to be below the threshold 504, triggers the activation of the injector unit 505 and an emergency call with the wearer's GPS coordinates 506.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. A wearable system for detecting an opioid overdose and automatically administering to a wearer a dosage injection of an opioid antidote, the system comprising:
   a wearable monitor unit, comprising one or more biometric monitors, a GPS receiver, a monitor microprocessor, and a wireless telephone transmitter;
   a wearable injector unit, comprising a solenoid switch, an electrical power source, a solenoid having an armature and a solenoid core, a syringe containing a prescribed dosage of the opioid antidote, a hypodermic needle, and a syringe assembly, wherein the syringe has a plunger and an outlet of the syringe is connected to the hypodermic needle through a flexible connection tubing, and wherein the syringe assembly comprises at least one plunger spring connected to the plunger and a release latch connected to the plunger, and wherein the solenoid is electrically connected to the electrical power source through the solenoid switch;
   wherein the injector unit further comprises a needle carriage, which carries the hypodermic needle along a carriage track, and wherein the armature of the solenoid has a proximal end, which is closer to the solenoid core, and a distal end, which is further from the solenoid core, and wherein the distal end of the armature is connected to the needle carriage by a carriage bracket;
   wherein the monitor unit is configured to be attached to the wearer, such that each of the biometric monitors continuously monitors wearer biometric data and continuously transmits the wearer biometric data to the monitor microprocessor;
   wherein the monitor microprocessor is programmed to continuously compare the wearer biometric data with one or more pre-set thresholds indicative of an opioid overdose;
   wherein the monitor microprocessor is programmed, upon determining that the wearer biometric data is indicative of an opioid overdose, to obtain current wearer location coordinates from the GPS receiver and to send one or more emergency messages, including the current wearer location coordinates, to one or more emergency contacts using the wireless telephone transmitter;
   wherein the monitor microprocessor is programmed, upon determining that the wearer biometric data is indicative of an opioid overdose, to transmit an activation signal to the solenoid switch of the injector unit;
   wherein, upon receiving the activation signal, the solenoid switch is configured to complete an energizing circuit, such that the electrical power source energizes the solenoid of the injector unit;
   wherein the injector unit is configured so that, when the solenoid is energized, the distal end of the armature, acting though the carriage bracket, pulls the needle carriage toward a needle aperture, through which the hypodermic needle protrudes and inserts into the wearer;

wherein the injector unit is configured so that, upon the solenoid being energized, the armature opens the release latch, thereby releasing the plunger and causing the plunger springs to fully depress the plunger, so as to force the prescribed dosage of the opioid antidote out of the syringe, through the connection tubing, into the hypodermic needle, and through the hypodermic needle into the wearer;

wherein the injector unit is configured, at an end of a dosage injection, to open the energizing circuit, such that the electrical power source ceases to energize the solenoid and the solenoid is de-energized; and wherein the injector unit is configured, upon the solenoid being de-energized, to retract the hypodermic needle, such that the syringe ceases to inject the opioid antidote into the wearer.

2. The system according to claim 1, wherein the solenoid further comprises a return spring, and wherein the solenoid is configured so that the armature is magnetically drawn into the solenoid core when the solenoid is energized, and wherein the solenoid is configured so that the return spring is biased when the armature is magnetically drawn into the solenoid core, and wherein the solenoid is configured so that, when the solenoid is de-energized, the armature ceases to be magnetically drawn into the solenoid core, and the return spring pulls the armature out of the solenoid core.

3. The system according to claim 2, wherein the syringe has a distal end, which is closer to the outlet of the syringe, and a proximal end, which is further from the outlet of the syringe, and wherein the syringe assembly further comprises a syringe switch on the distal end of the syringe, and wherein the syringe switch is configured, upon the plunger being fully depressed at an end of the dosage injection, to open the energizing circuit and to de-energize the solenoid, so that the return spring pulls the armature out of the solenoid core, and so that the armature, acting through the carriage bracket, pulls the needle carriage away from the needle aperture, thereby extracting the needle from the wearer.

4. The system according to claim 2, wherein the syringe has a distal end, which is closer to the outlet of the syringe, and a proximal end, which is further from the outlet of the syringe, and wherein the injector unit further comprises an injector microprocessor, which controls the solenoid switch, and wherein the syringe assembly further comprises a syringe sensor on the distal end of the syringe, and wherein the syringe sensor communicates with the injector microprocessor, and wherein the syringe sensor is configured, upon the plunger being fully depressed at an end of the dosage injection, to signal the injector microprocessor to control the solenoid switch so as to open the energizing circuit and de-energize the solenoid, so that the return spring pulls the armature out of the solenoid core, and so that the armature, acting through the carriage bracket, pulls the needle carriage away from the needle aperture, thereby extracting the needle from the wearer.

5. The system according to any one of claims 1-2 and 3-4, wherein the monitor unit and the injector units are combined in a single wearable monitor and injector unit that is attachable to the wearer at a single location.

6. The system according to any one of claims 1-2 and 3-4, wherein the monitor unit and the injector units are separate units that are attachable to the wearer at two separate locations.

7. The system according to claim 6, wherein the solenoid switch is a wireless switch, and wherein the monitor microprocessor is programmed, upon determining that the wearer biometric data is indicative of an opioid overdose, to wirelessly transmit the activation signal to the solenoid switch of the injector unit.

* * * * *